United States Patent
Wagner

Patent Number: 6,139,558
Date of Patent: Oct. 31, 2000

[54] ORAL HYGIENE APPLIANCE

[75] Inventor: Eugene C. Wagner, Pacific Palisades, Calif.

[73] Assignee: Dental Concepts LLC, Paramus, N.J.

[21] Appl. No.: 09/268,020

[22] Filed: Mar. 15, 1999

[51] Int. Cl.[7] .................................................. A61B 17/24
[52] U.S. Cl. ............................................. 606/161; 132/322
[58] Field of Search ...................................... 606/160, 161, 606/162; 433/89; 132/322

[56] References Cited

U.S. PATENT DOCUMENTS

| | | |
|---|---|---|
| D. 243,422 | 2/1977 | Varga . |
| D. 309,528 | 7/1990 | Valenti . |
| D. 332,352 | 1/1993 | Caldwell et al. . |
| 3,943,592 | 3/1976 | Bhaskar et al. . |
| 4,079,478 | 3/1978 | Andrews, Sr. . |
| 4,155,663 | 5/1979 | Cerquozzi . |
| 4,582,075 | 4/1986 | O'Neal et al. . |
| 5,226,197 | 7/1993 | Nack et al. . |
| 5,638,810 | 6/1997 | Yavitz . |
| 5,735,864 | 4/1998 | Heisinger, Jr. . |
| 5,774,925 | 7/1998 | Pryor, III . |
| 5,779,654 | 7/1998 | Foley et al. . |
| 5,916,228 | 6/1999 | Ripich et al. ........................... 606/161 |
| 5,967,152 | 10/1999 | Rimkus ................................ 606/161 |

*Primary Examiner*—Michael Buiz
*Assistant Examiner*—Jonathan D. Goldberg
*Attorney, Agent, or Firm*—Natter & Natter

[57] ABSTRACT

An oral hygiene appliance for cleansing the dorsum by both scraping and irrigation includes an irrigational applicator having a bored stem, the proximal end of which is connected to the mouth of a container filled with an irrigating medium. The distal end of the stem includes an open head configured with a transverse blade supported by a pair of diverging struts. A surface of the blade is roughened for scraping the dorsum. The distal end of the stem includes a nozzle with irrigating medium being discharged onto the dorsum surface on the labial side of the blade when the container is squeezed.

20 Claims, 2 Drawing Sheets

ORAL HYGIENE APPLIANCE

BACKGROUND OF THE INVENTION

1. Field of the Invention

The present invention relates generally to oral hygiene appliances and more specifically to devices which promote oral hygiene by removing debris from one's tongue.

2. Antecedents of the Invention

The general public has been highly conscious of oral hygiene, not only from a social standpoint, but in its relationship to overall health. While basic oral hygiene devices, such as toothbrushes, toothpaste, tooth powder, interdental stimulators, interproximal brushes, dental floss, toothpicks and dental picks, e.g. U.S. Pat. No. 4,326,548, have been in use through the years, in recent years there has been a proliferation of do-it-yourself oral hygiene cosmetic products, including various tooth whitening preparations, e.g. U.S. Pat. No. 5,084,268 as well as tooth polishers, for improvement of the appearance of one's mouth.

The public is also cognizant of the need to combat mouth malodor in daily social encounters. Various factors have been attributed to the generation of oral malodor, including improper brushing, failure to brush and/or failure to floss. Other factors include the presence of various compounds in the oral cavity which are alleged to cause malodor, such as hydrogen sulfide.

It has also been recognized that minute food particles and debris as well as odor producing bacteria reside on the tongue, particularly on the dorsal (upper) surface thereof, i.e. the dorsum.

The dorsum may be characterized as a rough surface which is covered with papillae. The anterior of the dorsum is covered with fungiform papillae and the posterior (pharyngeal) surface is covered with fungiform papillae interspersed with filiform papillae.

Food particles and the breakdown products of foods are trapped in crevices between the papillae. Dense bacterial populations and the many bacterial species resident on the dorsum colonize. It is believed that the dorsum is the source of most of the bacteria in the oral cavity and the source of oral malodor.

The prevalent use of mouthwashes, breath mints and breath sprays does not alleviate or reduce the source of malodor, but merely serves to mask the condition.

Various tongue scrapers such as those disclosed in the patents to Heisinger (U.S. Pat. No. 5,735,864), Andrews (U.S. Pat. No. 4,079,478), Nack (U.S. Pat. No. 5,226,179) and Bhaskar (U.S. Pat. No. 3,943,592) are among the devices which have been suggested for cleaning the tongue to remove food debris and other material accumulated on the dorsum.

Although such devices were capable of scraping the dorsum and loosening debris accumulated thereon, absent was the ability to flush the dorsum surface to assure complete cleansing. Further, none of these devices gained consumer acceptance either because they were too difficult to use, to costly to manufacture or were otherwise unsuited for general use.

SUMMARY OF THE INVENTION

The oral hygiene appliance of the present invention comprises an applicator having a hollow stem. A proximal end of the stem is connected to the mouth of a squeeze bottle filled with a suitable irrigating medium. Axially spaced from a distal end of the stem is an open head formed of an arched transverse blade, supported by a pair of struts.

The struts project from the distal end of the stem, with distal ends of the struts being joined to opposite ends of the blade. The lower surface of the blade is roughened for scraping contact with the dorsum. Extending through the longitudinal axis of the stem is a bore having a nozzle at the distal end of the stem.

The applicator is grasped by the squeeze bottle, which serves as a handle, and the blade is placed on the dorsum. The surface of the dorsum is scraped by the roughened surface of the blade when the applicator is moved back and forth along the dorsum, or in oval, circular or diagonal patterns. Simultaneously, the hand grasping the squeeze bottle exerts pressure on the bottle to force the irrigating medium onto the dorsal surface toward the blade to coact with the blade in lifting debris from the dorsum and flush the debris which has been scraped from the dorsum.

If in liquid form, the irrigating medium drains from the dorsum surface by either cascading over the struts, if the struts are placed against the dorsum, or if the struts are spaced from the dorsum, beneath the struts and out of the user's mouth.

The irrigating medium may comprise a liquid such as water, either alone or in combination with flavoring agents, an antibacterial agent, an antiseptic or an oxidizing agent, such as a solution of stabilized chlorine dioxide or hydrogen peroxide. Viscous semiliquid irrigating media such as gels or pastes are also employable. Such media are extruded from the bottle and onto the dorsum. In such instances, removal from the oral cavity entails rinsing with water or other liquid to flush the medium and debris.

From the foregoing compendium, it will be appreciated that it is an aspect of the present invention to provide an oral hygiene appliance of the general character described which is not subject to the disadvantages of the antecedents of the invention aforementioned.

A feature of the present invention is to provide an oral hygiene appliance of the general character described which is effective in the treatment of a source of oral malodor.

A consideration of the present invention is to provide an oral hygiene appliance of the general character described which is well suited to promote overall oral hygiene and reduce the rate of plaque formation in the oral cavity.

A further aspect of the present invention is to provide an oral hygiene appliance of the general character described which is simple to use.

A still further feature of the present invention is to provide a self contained oral hygiene appliance of the general character described which is well suited to effectively dislodge debris from surfaces of the dorsum and flush the debris from the oral cavity.

Another consideration of the present invention is to provide an oral hygiene appliance of the general character described which is portable and well suited for carrying about one's person for routine usage away from home.

Another feature of the present invention is to provide an oral hygiene appliance of the general character described which is disposable and hence well suited for one time usage by hotel guests and the like as well as for promotional use.

It is a further aspect of the present invention to provide an oral hygiene appliance of the general character described which is equally well suited for refilling with irrigating medium, either acquired in bulk or supplied in individual refill containers.

To provide an oral hygiene appliance of the general character described which is relatively low in cost and well suited for economic mass production fabrication is a further consideration of the present invention.

Yet another aspect of the present invention is to provide an oral hygiene appliance of the general character described which is well suited to utilize any of a number of available irrigating media or combinations thereof for efficacious cleansing of the oral cavity and for treatment of oral malodor.

An additional feature of the present invention is to provide an oral hygiene appliance of the general character described having a manipulating handle which carries a supply of irrigating medium.

Other aspects features and considerations in part will be obvious and in part will be pointed out hereinafter.

With these ends in view, the invention finds embodiment in certain combinations of elements, arrangements of parts and series of steps by which the aforesaid aspects, features and considerations and certain other aspects, features and considerations are attained, all with reference to the accompanying drawings and the scope of which will be more particularly pointed out and indicated in the appended claims.

BRIEF DESCRIPTION OF THE DRAWINGS

In the accompanying drawings, wherein are shown some of the various possible exemplary embodiments of the invention.

DESCRIPTION OF THE PREFERRED EMBODIMENTS

Figure 1:
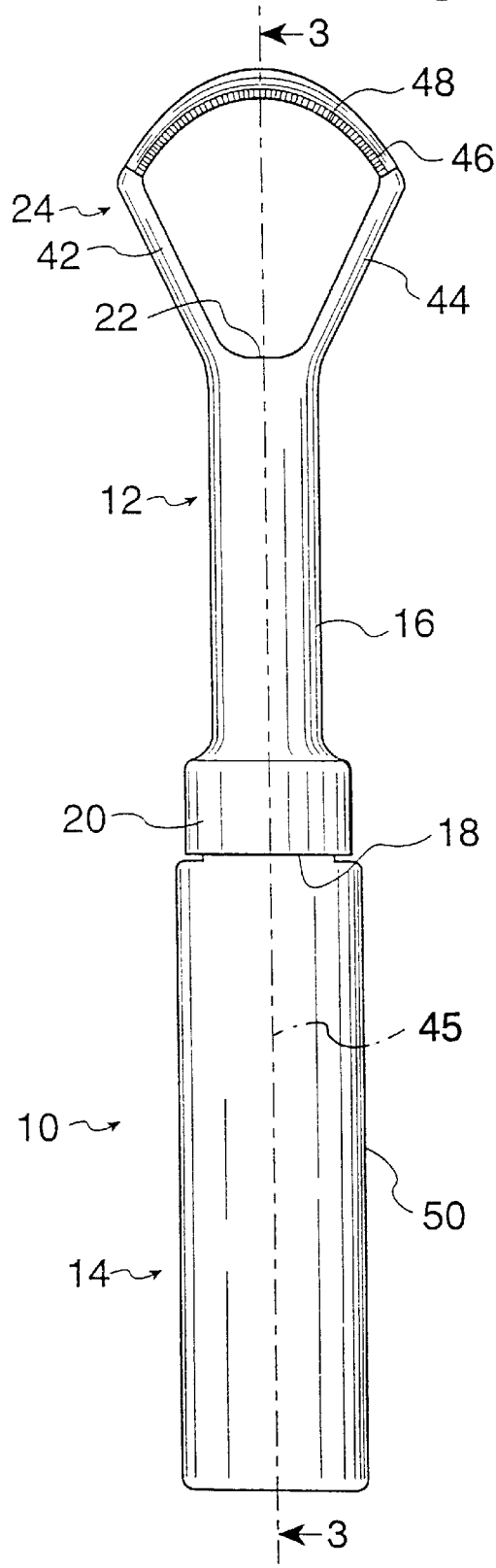
FIG. 1 is front elevation view of an oral hygiene appliance constructed in accordance with and embodying the invention and showing an applicator including a hollow stem and an open head having an arched transverse scraper blade spaced from a distal end of the stem.

Referring now in detail to the drawings, the reference numeral 10 denotes generally an oral hygiene appliance constructed in accordance with and embodying the invention. The appliance 10 comprises an applicator 12 and a handle 14.

Figure 5:
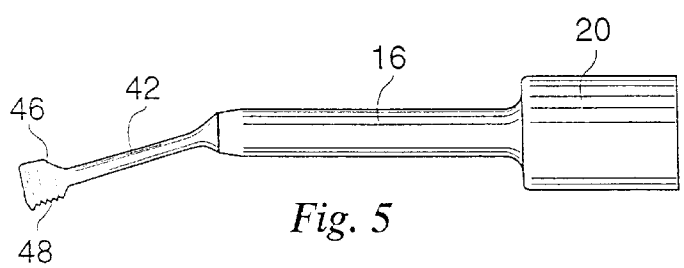
FIG. 5 is a side elevational view of the applicator.

The applicator 12 includes an elongate stem 16 having, at its proximal end 18, an enlarged cylindrical skirt 20 and at a distal end 22, a dorsal engagement section 24. The stem 16 may be configured to have a width greater than its thickness, as will be noted from a comparison of FIG. 1 with FIG. 5.

Figure 3:
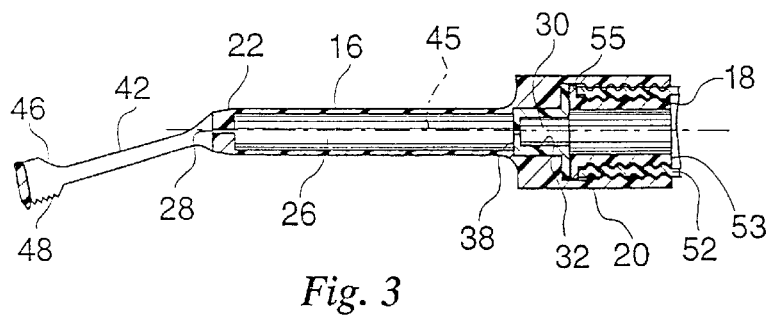
FIG. 3 is a fragmentary sectional view of the appliance, the same being taken substantially along the plane 3—3 of FIG. 1 and showing a hollow bore extending from the skirt to a reduced diameter nozzle at the distal end of the stem.

From an observation of FIG. 3, it will be noted that a cylindrical bore 26 extends from the skirt 20 to a constricted nozzle orifice 28 at the distal end 22. The bore 26 is enlarged adjacent the proximal end 18 to provide a socket 30 which receives a check valve 32.

The check valve 32 includes an annular radial flange 34 having a diameter suitable to be seated within the skirt 20 and a cylindrical neck 36 having a transverse diaphragm end 38. Formed in the end 38 are a pair of intersecting slits 40. The diaphragm end of the check valve 32 opens to permit flow from the skirt 20 through the bore 26 and closes to prevent back flow in the opposite direction.

The dorsal engagement section 24 comprises an open head having a pair of struts 42, 44 which diverge from opposite sides of the stem 16 at the distal end 22. The struts 42, 44 extend forwardly as viewed in FIG. 1 and downwardly at an angle of approximately 10 to 15 degrees (as viewed in FIG. 3) from the longitudinal axis of the stem, designated by the reference numeral 45.

Figure 2:
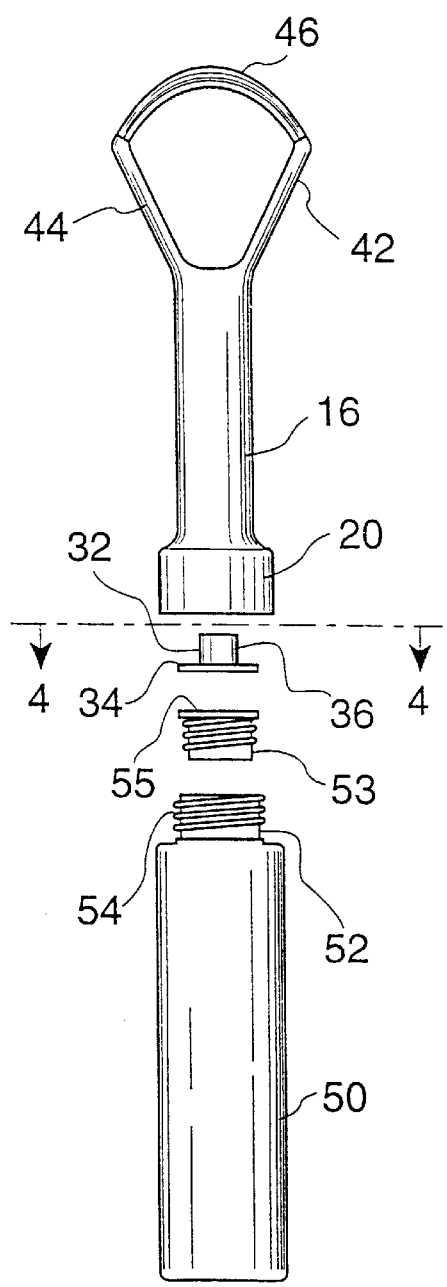
FIG. 2 is a reduced scale rear elevation exploded view of the appliance and showing a check valve positioned between a neck of a squeeze bottle handle and a skirt at a proximal end of the stem.
Figure 4:
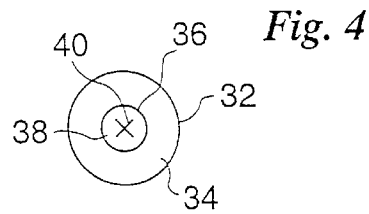
FIG. 4 is a top plan view of the check valve, the same being taken substantially along the plane 4—4 of FIG. 2.

An arcuately curved integral transverse blade 46 is supported from the distal ends of the struts 44, 42 such that the dorsal engagement section 24 assumes a generally triangular configuration as shown in FIG. 1 and FIG. 2.

The lowermost edge of the blade 46 (as viewed in FIG. 3 and FIG. 5) is roughened as by a plurality of serrations 48 for the purpose of scraping the dorsum in accordance with the invention as will be described in greater detail hereinafter.

Pursuant to the invention, the handle 14 is formed of a plastic squeeze bottle 50 having a mouth 52 with threads 54 which engage mating threads 56 of the skirt 20. The mouth 50 may be reinforced by a threaded sleeve 53 which includes external threads mating with internal threads of the mouth which are registered with the threads 54.

The check valve flange 34 may function as a gasket to assure a liquid tight seal between a peripheral lip 55 of the sleeve 53 at a rim of the bottle mouth 52 and the skirt 20.

In accordance with the invention, the handle 14 is grasped in one hand and the roughened surface 48 of the blade 46 is urged against the dorsum for removal of dorsal debris. In use, a back and forth, circular or irregular scraping pattern may be employed.

Simultaneous with the scraping of the dorsum with the roughened surface of the blade 46, the user squeezes the bottle 50 to force irrigating medium from the bottle 50 through the check valve 32, the bore 26 and out of the nozzle orifice 28 in a stream, spray or drop pattern as determined by the nozzle orifice configuration, the viscosity of the medium and the pressure applied to expel the medium. The medium is deposited on the surface of the dorsum on the labial side of the blade 46.

The irrigating medium serves to flush the debris scraped from the dorsum out of the oral cavity by carrying such debris with its discharge flow. Further, the irrigating medium may cooperate with the blade 46 to assist in lifting debris from the dorsum.

If the struts have been placed against the dorsum while the dorsum is being scraped with the blade 46, drainage of a liquid irrigating medium will occur by cascading downwardly and outwardly over the struts, while if the struts are not in contact with the dorsum, the drainage flow will occur under the struts.

When the irrigating medium is a viscous material, it is voided from the oral cavity, together with debris carried in the medium, by rinsing the oral cavity.

Antiseptic and/or antibacterial and/or oxidizing agents in the irrigating medium serve to retard bacterial growth on the dorsum. Routine usage of the invention will assure retarded bacterial growth with resultant absence of oral malodor.

The appliance 12 is well suited for single use, while it equally lends itself to multiple usage with replacement bottles 50 filled with irrigating medium. In fact, the invention may be offered as a kit with, for example, a one week supply of irrigating medium prepackaged in several bottles.

Optionally, the kits may be offered with different formulations of irrigating medium. For example, kits may be offered with a supply of irrigating medium having only specified flavoring agents or specified antibacterial agents, with the user ultimately selecting, from a variety of irrigating medium formulations, the one most effective.

It should further be appreciated that this invention should not be interpreted as being limited to implementation in a squeeze bottle format only. Applicator handles may be configured for carrying an irrigating medium and forcing or, as the case may be, extruding the medium through the applicator stem with a manual squeeze pump or even a battery-powered electric pump.

Figure 6:
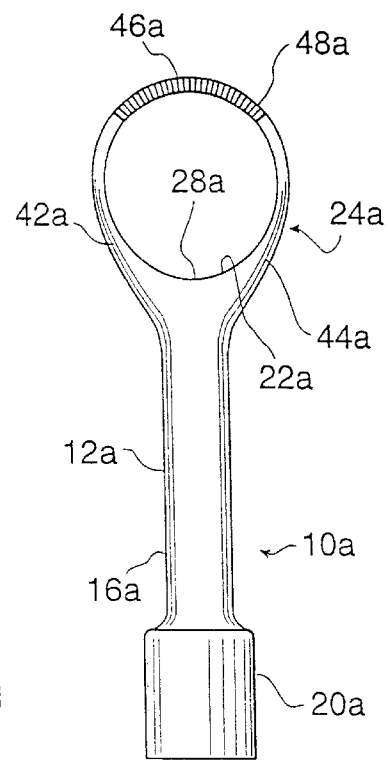
FIG. 6 is a fragmentary front elevational view of an alternate embodiment of the applicator, wherein a blade is incorporated in an elliptical head.

Referring now to FIG. 6 wherein an alternate embodiment of the invention is shown, like numerals will be employed to denote like components of the previous embodiment, however bearing the suffix "a". In FIG. 6 there is disclosed an appliance 10a which includes an applicator 12a having a stem 16a with an enlarged skirt 20a at one end and a nozzle orifice 28a at its other end.

A squeeze bottle 50a carrying an irrigating medium is threadingly secured to the stem 16a at the skirt 20a. In all respects, the embodiment of FIG. 6 is identical to the previous embodiment except for the configuration of a dorsal engagement section 24a.

The dorsal engagement section 24a of this embodiment comprises an open head wherein a curved blade 46a is smoothly incorporated in an ellipsoid having a pair of curved longitudinal spans 42a, 44a. A distal end 22a of the stem is configured with a continuous internal curve compatible with the ellipsoid.

A lower dorsum engaging surface of the blade 46a is roughened for scraping at an area 48a in a manner similar to that of the previous embodiment.

Thus it will be seen that there is provided an oral hygiene appliance which achieves the various aspects, features and considerations of the present invention and which is well suited to meet the conditions of practical usage.

Since various possible embodiments might be made of the present invention and since various changes might be made in the exemplary embodiments shown herein without departing from the spirit of the invention, it should be understood that all matter herein described or shown in the accompanying drawings should be interpreted as illustrative and not in a limiting sense.

What is claimed is:

1. An oral hygiene appliance, comprising a stem having an axis, a handle at one end of the stem, the handle storing a supply of irrigating medium, a bore extending through the stem, the bore being in communication with the supply of irrigating medium, a nozzle at an other end of the stem, the nozzle having an axis coincident with the axis of the stem, the nozzle being in communication with the bore, the oral hygiene appliance further including a dorsal engagement section at the other end of the stem, the dorsal engagement section including a blade, the blade being configured to scrape the dorsum of a user when manipulated through movement of the handle, the blade being fixed with respect to the other end of the stem, the blade being spaced from the nozzle, the blade extending in a plane generally transverse to the axis of the nozzle, whereby the supply of irrigating medium is discharged through the nozzle and toward the blade.

2. An oral hygiene appliance as constructed in accordance with claim 1 wherein the blade is curved.

3. An oral hygiene appliance as constructed in accordance with claim 1 wherein the blade includes a roughened surface for scraping engagement with the dorsum.

4. An oral hygiene appliance as constructed in accordance with claim 1 wherein the dorsal engagement section includes a pair of struts extending from the other end of the stem, each strut being joined to an end of the blade.

5. An oral hygiene appliance as constructed in accordance with claim 1 wherein the handle comprises a bottle.

6. An oral hygiene appliance as constructed in accordance with claim 5 wherein the bottle includes a threaded mouth, the stem includes a threaded skirt at the one end and the threaded mouth is engaged in the threaded skirt.

7. An oral hygiene kit, including an oral hygiene appliance as constructed in accordance with claim 5, the oral hygiene kit further including a plurality of bottles each filled with the supply of irrigating medium, successive bottles of the plurality being employed as replacement handles upon depletion of the supply of irrigating medium contained in each bottle.

8. An oral hygiene appliance as constructed in accordance with claim 1 wherein the dorsal engagement section is generally ellipsoidal in shape.

9. An oral hygiene appliance, comprising a stem having an axis, a handle at one end of the stem, the handle carrying a supply of irrigating medium, a bore extending through the stem, the bore being in communication with the supply of irrigating medium, a check valve, the check valve being positioned between the handle and the bore, the check valve permitting flow of the supply of irrigating medium from the handle into the bore and preventing reverse flow into the handle, a nozzle at an other end of the stem, the nozzle being in communication with the bore, the oral hygiene appliance further including a dorsal engagement section at the other end of the stem, the dorsal engagement section including a scraping blade, the scraping blade being fixed with respect to the other end of the stem, the scraping blade being spaced from the nozzle, the scraping blade extending in a direction generally transverse to the axis of the stem.

10. An oral hygiene appliance as constructed in accordance with claim 1 wherein the supply of irrigating medium includes an antibacterial agent.

11. An oral hygiene appliance as constructed in accordance with claim 1 wherein the supply of irrigating medium includes a flavoring agent.

12. An oral hygiene appliance as constructed in accordance with claim 1 wherein the supply of irrigating medium includes an antiseptic agent.

13. An oral hygiene appliance as constructed in accordance with claim 1 wherein the stem is rigidly joined to the handle.

14. An oral hygiene appliance as constructed in accordance with claim 1 wherein at least a portion of the handle is squeezable to expel the supply of stored irrigating medium from the handle through the bore and from the bore through the nozzle.

15. A self contained dorsal scraper and irrigator appliance, the appliance including a handle comprising a squeeze bottle, the squeeze bottle carrying a supply of irrigating medium, a dorsal scraper blade and a rigid coupling attached to the bottle, the scraper blade being rigidly fixed to the coupling and the coupling being rigidly fixed to the bottle, the coupling having a nozzle for discharge of irrigating medium carried in the bottle, the nozzle being spaced from the blade, the irrigating medium being forced from the bottle, through the nozzle and onto the dorsum on a labial side of the blade when the bottle is squeezed.

16. A treatment method for alleviating an oral malodor condition in the oral cavity with a self contained dorsal scraper and irrigator appliance as constructed in accordance with claim 15, the method comprising the steps of:
   a) grasping the squeeze bottle with one hand,
   b) inserting the dorsal scraper blade in the oral cavity,
   c) contacting the dorsal scraper dorsum with the blade,
   d) scraping the dorsum by manipulating the squeeze bottle to move the dorsal scraper blade along the surface of the dorsum, and
   e) irrigating the dorsum by squeezing the squeeze bottle to discharge the supply of irrigating medium from the nozzle and onto the surface of the dorsum on the labial side of the dorsal scraper blade.

17. A method of treatment in accordance with claim 16 wherein the dorsal scraper blade includes a roughened surface, the step of contacting the dorsum with the dorsal scraper blade including the step of contacting the dorsum with the roughened surface of the dorsal scraper blade.

18. A method of treatment in accordance with claim 16 wherein the step of scraping the dorsum includes manipulating the squeeze bottle to move the dorsal scraper blade in a back and forth motion.

19. A self contained dorsal scraper and irrigator appliance as constructed in accordance with claim 15 wherein the nozzle includes an axis, the nozzle axis being substantially perpendicular to a plane within which the blade is situated, the supply of irrigating medium being forced through the nozzle and toward the blade.

20. An oral hygiene appliance, comprising a stem having an axis, a handle at one end of the stem, the handle storing a supply of irrigating medium, a bore extending through the stem, the stem being rigidly joined to the handle, the bore being in communication with the supply of irrigating medium stored in the handle, a nozzle another end of the stem, the nozzle having an axis coincident with the axis of the stem, the nozzle being in communication with the bore, at least a portion of the handle being squeezable to expel the supply of stored irrigating medium from the handle through the bore and from the bore through the nozzle, the oral hygiene appliance further including a dorsal engagement section at the other end of the stem, the dorsal engagement section including a scraping blade, the scraping blade being fixed with respect to the other end of the stem, the scraping blade being spaced from the nozzle, the scraping blade extending in a direction generally transverse to the axis of the nozzle.

* * * * *